US011571200B2

United States Patent
Burkhart et al.

(10) Patent No.: US 11,571,200 B2
(45) Date of Patent: *Feb. 7, 2023

(54) METHOD FOR KNOTLESS FIXATION OF TISSUE

(71) Applicant: Arthrex, Inc., Naples, FL (US)

(72) Inventors: Stephen S. Burkhart, San Antonio, TX (US); Peter J. Dreyfuss, Naples, FL (US); Neil S. ElAttrache, Los Angeles, CA (US)

(73) Assignee: Arthrex, Inc., Naples, FL (US)

(*) Notice: Subject to any disclaimer, the term of this patent is extended or adjusted under 35 U.S.C. 154(b) by 266 days.

This patent is subject to a terminal disclaimer.

(21) Appl. No.: 15/976,157

(22) Filed: May 10, 2018

(65) Prior Publication Data

US 2018/0256155 A1 Sep. 13, 2018

Related U.S. Application Data

(63) Continuation of application No. 14/707,861, filed on May 8, 2015, now Pat. No. 10,881,388, which is a (Continued)

(51) Int. Cl.
*A61B 17/04* (2006.01)
*A61F 2/08* (2006.01)

(52) U.S. Cl.
CPC ........ *A61B 17/0401* (2013.01); *A61F 2/0805* (2013.01); *A61F 2/0811* (2013.01);
(Continued)

(58) Field of Classification Search
CPC ........ A61B 2017/0409; A61B 17/0401; A61B 17/88; A61B 17/7074; A61B 17/7076;
(Continued)

(56) References Cited

U.S. PATENT DOCUMENTS 4,484,570 A 11/1984 Sutter et al.
4,870,957 A 10/1989 Goble
(Continued)

FOREIGN PATENT DOCUMENTS

EP 1 857 054 A2 11/2007
WO WO 2006/060035 A2 6/2006
WO WO 2006/099109 A2 9/2006

*Primary Examiner* — Diane D Yabut
*Assistant Examiner* — Christina C Lauer
(74) *Attorney, Agent, or Firm* — Blank Rome LLP

(57) ABSTRACT

A swivel suture anchor for knotless fixation of tissue. The suture anchor includes an anchor tip configured to capture suture, the anchor tip being rotatably received within a fixation device upon advancement of the fixation device over a shaft of the anchor tip. The anchor tip is configured to receive a suture to be anchor in bone without requiring suture knots. The anchor tip can be a conical metal tip which is self-punching and avoids the need for pre-drilling a hole in bone. The anchor tip includes a closed aperture to allow free sliding of a suture strand. The suture is secured in a hole in bone by inserting the anchor tip into bone, and advancing a fenestrated fixation device, such as a cannulated interference screw, over a shaft of the anchor tip.

32 Claims, 11 Drawing Sheets

Related U.S. Application Data continuation of application No. 13/403,366, filed on Feb. 23, 2012, now abandoned, which is a continuation of application No. 12/418,391, filed on Apr. 3, 2009, now abandoned, which is a continuation-in-part of application No. 12/368,946, filed on Feb. 10, 2009, now abandoned, which is a continuation-in-part of application No. 12/043,008, filed on Mar. 5, 2008, now abandoned, which is a continuation-in-part of application No. 11/802,057, filed on May 18, 2007, now Pat. No. 9,005,246, said application No. 12/368,946 is a continuation-in-part of application No. 11/392,798, filed on Mar. 30, 2006, now Pat. No. 7,803,173.

(60) Provisional application No. 60/801,097, filed on May 18, 2006, provisional application No. 60/666,518, filed on Mar. 30, 2005.

(52) U.S. Cl.
CPC .. *A61B 2017/044* (2013.01); *A61B 2017/0409* (2013.01); *A61B 2017/0414* (2013.01); *A61B 2017/0438* (2013.01); *A61B 2017/0445* (2013.01); *A61B 2017/0458* (2013.01); *A61B 2017/0459* (2013.01); *A61F 2002/0817* (2013.01); *A61F 2002/0841* (2013.01); *A61F 2002/0852* (2013.01); *A61F 2002/0858* (2013.01); *A61F 2002/0888* (2013.01)

(58) Field of Classification Search
CPC ........ A61B 17/7082; A61B 2017/0414; A61B 2017/044; A61B 2017/0441; A61B 2017/0443; A61B 2017/0455; A61B 2017/0446; A61B 2017/0448; A61B 2017/045; A61B 2017/0453; A61B 2017/0454; A61B 2017/0456; A61B 2017/0458; A61B 2017/0459; A61F 2002/0858; A61F 2002/0847; A61F 2002/0864
See application file for complete search history.

(56) References Cited

U.S. PATENT DOCUMENTS

| | | |
|---|---|---|
| 5,084,050 A | 1/1992 | Draenert |
| 5,129,904 A | 7/1992 | Illi |
| 5,152,790 A * | 10/1992 | Rosenberg ............ A61F 2/0811 606/328 |
| 5,236,445 A * | 8/1993 | Hayhurst ............ A61B 17/0401 411/511 |
| 5,249,899 A | 10/1993 | Wilson |
| 5,258,016 A * | 11/1993 | DiPoto ............... A61B 17/0401 606/104 |
| 5,368,595 A * | 11/1994 | Lewis ................ A61B 17/0401 606/151 |
| 5,423,860 A | 6/1995 | Lizardi et al. |
| 5,500,000 A | 3/1996 | Feagin et al. |
| 5,540,718 A | 7/1996 | Bartlett |
| 5,545,180 A | 8/1996 | Le et al. |
| 5,827,285 A | 10/1998 | Bramlet |
| 5,860,973 A | 1/1999 | Michelson |
| 5,935,129 A | 8/1999 | McDevitt |
| 5,968,047 A | 10/1999 | Reed |
| 6,045,574 A | 4/2000 | Thal |
| 6,048,343 A | 4/2000 | Mathis et al. |
| 6,143,017 A | 11/2000 | Thal |
| 6,214,007 B1 | 4/2001 | Anderson |
| 6,355,043 B1 | 3/2002 | Adam |
| 6,368,326 B1 | 4/2002 | Dakin |
| 6,517,542 B1 * | 2/2003 | Papay ................ A61B 17/0401 606/232 |
| 6,527,794 B1 | 3/2003 | McDevitt et al. |
| 6,544,281 B2 | 4/2003 | ElAttrache et al. |
| 6,589,245 B1 | 7/2003 | Weiler et al. |
| 6,840,953 B2 | 1/2005 | Martinek |
| 6,863,671 B1 | 3/2005 | Strobel et al. |
| 6,939,135 B2 | 9/2005 | Sapian |
| 7,083,647 B1 | 8/2006 | Sklar et al. |
| 7,261,716 B2 | 8/2007 | Strobel et al. |
| 7,300,439 B2 | 11/2007 | May |
| 7,329,272 B2 | 2/2008 | Burkhart et al. |
| 7,572,283 B1 * | 8/2009 | Meridew ............ A61F 2/0805 606/232 |
| 7,585,311 B2 | 9/2009 | Green et al. |
| 7,588,587 B2 | 9/2009 | Barbieri et al. |
| 7,645,293 B2 | 1/2010 | Martinek et al. |
| 7,717,947 B1 | 5/2010 | Wilberg et al. |
| 7,803,173 B2 | 9/2010 | Burkhart et al. |
| 7,976,565 B1 * | 7/2011 | Meridew ........... A61B 17/0401 606/232 |
| 7,981,140 B2 | 7/2011 | Burkhart |
| 7,993,369 B2 | 8/2011 | Dreyfuss |
| 8,012,174 B2 | 9/2011 | ElAttrache et al. |
| 8,114,127 B2 | 2/2012 | West, Jr. |
| 8,663,279 B2 | 3/2014 | Burkhart et al. |
| 9,005,246 B2 | 4/2015 | Burkhart et al. |
| 2002/0013608 A1 * | 1/2002 | ElAttrache .......... A61F 2/0805 606/232 |
| 2002/0147463 A1 * | 10/2002 | Martinek ........... A61B 17/0401 606/232 |
| 2002/0156476 A1 * | 10/2002 | Wilford ................ A61F 2/0811 606/232 |
| 2003/0065332 A1 | 4/2003 | TenHuisen |
| 2003/0153947 A1 | 8/2003 | Koseki |
| 2004/0093030 A1 | 5/2004 | Cox et al. |
| 2004/0093031 A1 * | 5/2004 | Burkhart ............. A61F 2/0811 606/232 |
| 2004/0138706 A1 * | 7/2004 | Abrams ............. A61B 17/0401 606/232 |
| 2004/0193217 A1 | 9/2004 | Lubbers |
| 2004/0225292 A1 | 11/2004 | Sasso et al. |
| 2005/0119698 A1 | 6/2005 | Martinek |
| 2006/0004364 A1 | 1/2006 | Green et al. |
| 2006/0079904 A1 | 4/2006 | Thal |
| 2006/0100630 A1 | 5/2006 | West |
| 2006/0235413 A1 | 10/2006 | Denham et al. |
| 2006/0247642 A1 | 11/2006 | Stone et al. |
| 2006/0259076 A1 | 11/2006 | Burkhart et al. |
| 2007/0038221 A1 | 2/2007 | Fine et al. |
| 2007/0060922 A1 | 3/2007 | Dreyfuss |
| 2007/0135843 A1 | 6/2007 | Burkhart |
| 2007/0191849 A1 | 8/2007 | ElAttrache |
| 2007/0225719 A1 | 9/2007 | Stone et al. |
| 2008/0004659 A1 | 1/2008 | Burkhart et al. |
| 2008/0009904 A1 | 1/2008 | Bourque et al. |
| 2008/0154314 A1 | 6/2008 | McDevitt |
| 2008/0208253 A1 | 8/2008 | Dreyfuss et al. |
| 2008/0215091 A1 | 9/2008 | Dreyfuss |
| 2008/0275431 A1 | 11/2008 | Stone et al. |
| 2008/0281325 A1 | 11/2008 | Stone et al. |
| 2009/0192546 A1 | 7/2009 | Schmieding et al. |
| 2009/0281581 A1 | 11/2009 | Berg |
| 2009/0287259 A1 | 11/2009 | Trenhaile |
| 2010/0248888 A1 | 9/2010 | Hamperl |
| 2010/0249854 A1 | 9/2010 | Thomas |
| 2010/0331896 A1 | 12/2010 | Le Couedic et al. |
| 2011/0106252 A1 | 5/2011 | Barwood |
| 2011/0313455 A1 | 12/2011 | ElAttrache et al. |
| 2012/0022588 A1 | 1/2012 | Berg |
| 2012/0165868 A1 | 6/2012 | Burkhart et al. |
| 2013/0035721 A1 | 2/2013 | Brunelle |
| 2013/0158597 A1 | 6/2013 | Hernandez |
| 2013/0345750 A1 | 12/2013 | Sullivan |
| 2014/0364906 A1 | 12/2014 | Palese |
| 2017/0209139 A1 * | 7/2017 | Burkhart ........... A61B 17/0401 |

* cited by examiner

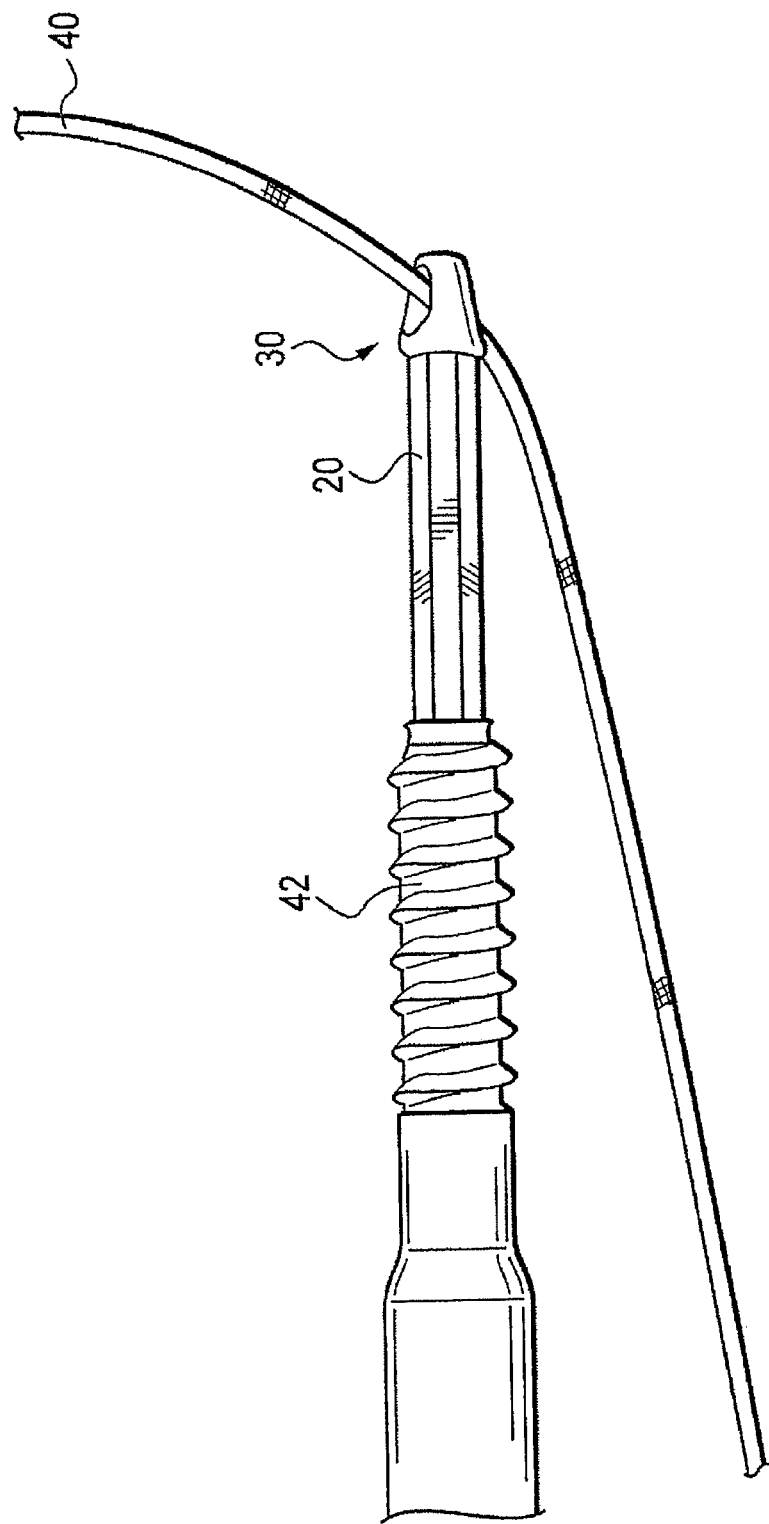

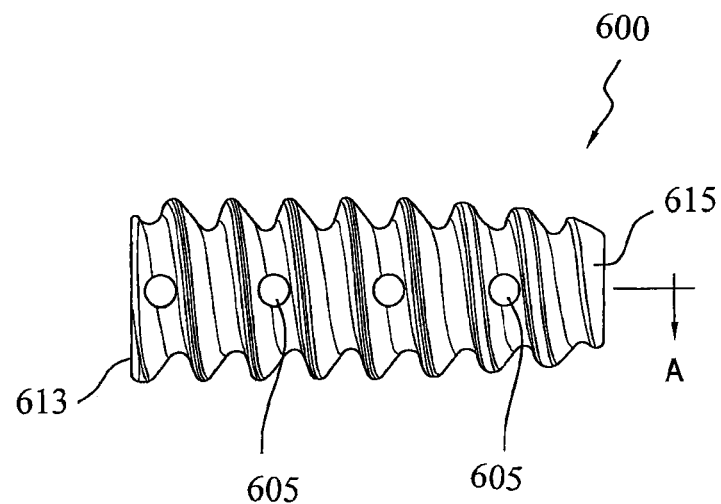
FIG. 14
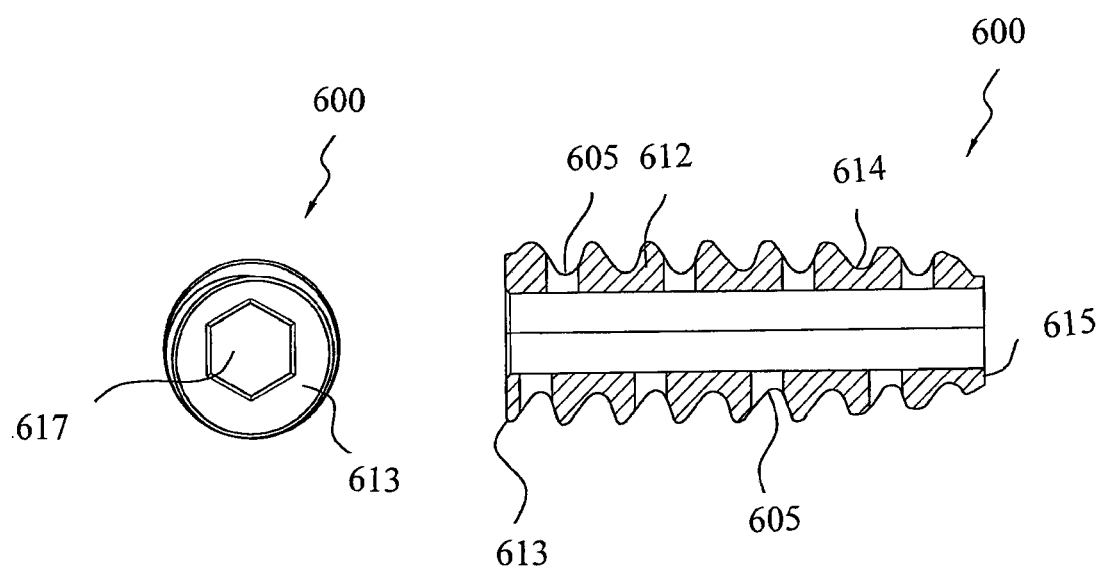
FIG. 15
FIG. 16

METHOD FOR KNOTLESS FIXATION OF TISSUE

This is a continuation of application Ser. No. 14/707,861, filed on May 8, 2015, which is a continuation of application Ser. No. 13/403,366, filed Feb. 23, 2012, now abandoned, which is a continuation of application Ser. No. 12/418,391, filed on Apr. 3, 2009, now abandoned, which is a continuation-in-part of application Ser. No. 12/368,946, filed on Feb. 10, 2009, now abandoned, which is a continuation-in-part of application Ser. No. 12/043,008, filed on Mar. 5, 2008, now abandoned, which in turn is a continuation-in-part of application Ser. No. 11/802,057, filed on May 18, 2007, now U.S. Pat. No. 9,005,246, which claims the benefit of Provisional Application No. 60/801,097, filed on May 18, 2006. Application Ser. No. 12/368,946, filed on Feb. 10, 2009, is also a continuation-in-part of application Ser. No. 11/392,798, filed on Mar. 30, 2006, now U.S. Pat. No. 7,803,173, which claims the benefit of Provisional Application No. 60/666,518, filed on Mar. 30, 2005. The entire disclosures of all of these priority applications are incorporated herein by reference.

FIELD OF THE INVENTION

The present invention relates to methods and instruments for fixation of sutures and tissue to bone.

BACKGROUND OF THE INVENTION

When soft tissue tears away from bone, reattachment becomes necessary. Various devices, including sutures, screws, staples, wedges, anchors and plugs have been used in the prior art to secure soft tissue to bone. Surgical methods utilizing suture anchors alone are disadvantageous for reattachment of large areas of detached tissue because they often do not allow good tissue to bone contact.

Reattachment of soft tissue to bone typically requires the surgeon to pass suture material through selected tissue, form a plurality of surgical knots extracorporeally and then move the knots into position adjacent the desired tissue to be sutured. In such procedures, the surgeon must manually tie the knots on the suture strands after the suture is threaded through the selected tissues to be sutured. Knot tying during surgery, particularly arthroscopic surgery, is tedious and time-consuming. There is also a tendency for the knots to deform or collapse as the surgeon manually forces the knots down into the proper position. Also, the suture knots often are exposed to abrasion or cutting by sharp or rough areas along the walls of the bone canal into which anchors are typically inserted to provide fixation of tendon to bone.

Accordingly, a need exists for an improved method for attaching soft tissue to bone which does not require multiple suture knots and which allows the tendon to remain securely in place until the ligaments naturally attach to bone. A need also exists for such a knotless method of attaching tissue to bone which employs an implant with a fenestrated configuration that promotes healing of tissue.

SUMMARY OF THE INVENTION

The instruments and methods of the present invention overcome the disadvantages of the prior art, such as those noted above, by providing a swivel implant at the distal end of a driver that securely engages and locks into a cannulated ribbed body of an interference plug or screw. The swivel implant includes a closed aperture for receiving a strand attached to a graft, such that the strand is able to freely slide through the aperture.

In one embodiment of the invention, the strand is passed through the graft at desired points. A cannulated plug or screw is pre-loaded onto a driver provided with a swivel lock twist-in anchor at its distal end. The strand attached to the graft is passed through the aperture of the swivel implant located at the distal end of the driver. The distal end of the driver together with the implant is inserted directly into the bone. The driver may be rotated (in a clockwise direction, for example) to advance a screw over the anchor to complete insertion. The cannulated plug or screw is provided with a plurality of openings or fenestrations of various dimensions and geometries to provide multiple pathways through the device (i.e., though the interior of the body and through the fenestrations) to allow blood to flow to increase the healing zone, for example, for rotator cuff repair, while also promoting bone in-growth.

Other features and advantages of the present invention will become apparent from the following description of exemplary embodiments of the invention described with reference to the accompanying drawings.

BRIEF DESCRIPTION OF THE DRAWINGS

FIGS. 12 and 13 provide additional illustrations of the swivel anchor assembly of the present invention, and the swivel anchor inserted in a bone socket, respectively.

FIGS. 14-16 illustrate various views of a fixation device with fenestrations and used in conjunction with the swivel anchor assembly of the present invention.

DETAILED DESCRIPTION OF THE PREFERRED EMBODIMENTS

The present invention provides apparatus and methods for knotless tissue fixation using a swivel anchor device.

Figure 1:
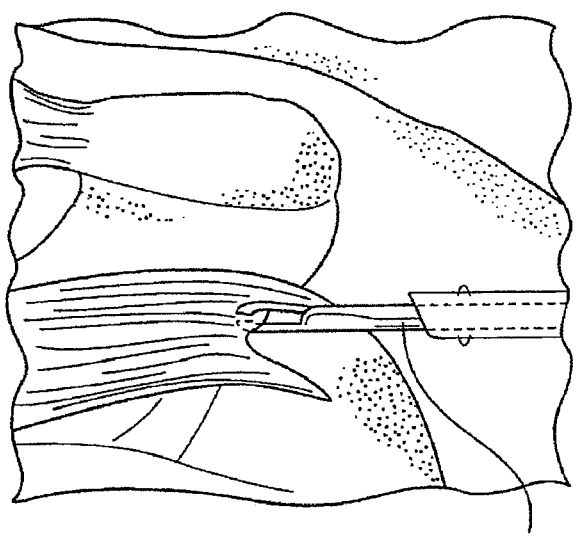
FIGS. 1-6 depict a series of steps of shoulder repair using a plurality of swivel anchor devices according to the present invention.

FIG. 1 illustrates a side view of a human shoulder of a patient undergoing a rotator cuff repair in accordance with an exemplary embodiment of the present invention. The patient may be positioned in the beach chair position using the Arthrex Beach Chair Lateral Traction Device or in a lateral decubitus position using the Arthrex 3-Point Shoulder Distraction System. Access to the subacromial space is facilitated with a variety of cannulas.

First, and as illustrated in FIG. 1, the mobility of the tear is assessed using, for example, a tissue grasper 10 such as the Arthrex KingFisher™ Suture Retriever/Tissue Grasper, to determine whether a U or L-shaped component exists. Where large tears extend to the superior aspect of the glenoid, margin convergence suturing is performed to reduce volume and strain on the repair. Subsequently, the length and width of the rotator cuff footprint is assessed and a bleeding bed for enhanced tendon to bone healing may be formed. This may be accomplished with a burr to perform a light dusting of the greater tuberosity, or by using a chondro pick to microfracture the footprint and maximize vascular channels.

Figure 2:
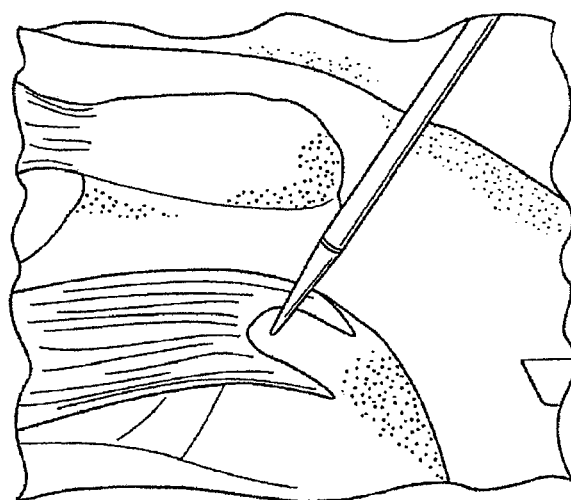

FIG. 2 illustrates the preparation of two pilot holes for two swivel anchors that will be inserted in the medial row. A punch may be employed adjacent to the articular margin of the humerus and at about 45° angle to form the two pilot holes.

Figure 3:
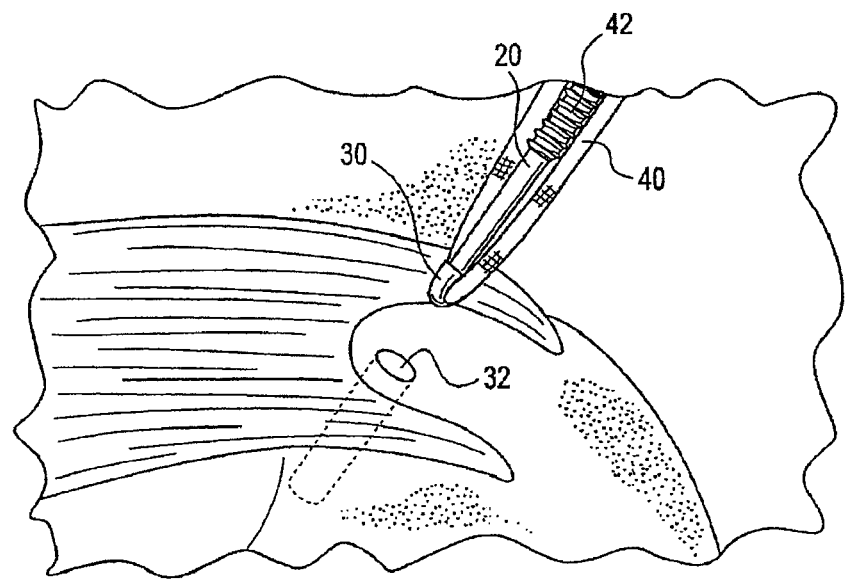
Figure 4:
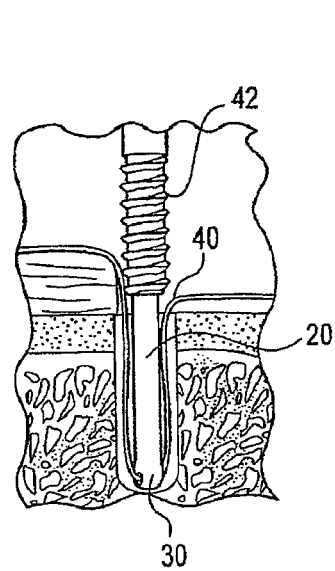
Figure 4A:
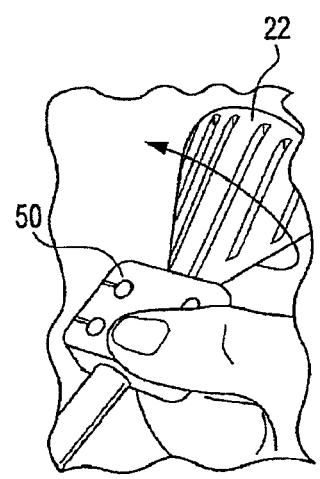

Subsequent to the formation of the pilot holes, and as shown in FIGS. 3 and 4, a swivel implant 30, loaded with a strand of suture tape 40, preferably Arthrex FiberTape, is placed in the medial pre-formed hole 32. Arthrex FiberTape is a high strength suture tape which is braided and rectangular-like in cross section and is disclosed in U.S. Pat. No. 7,892,256, the disclosure of which is incorporated by reference herein. However, the anchor of the present invention can be used with any type of flexible material or suture. The driver is then rotated to advance screw 42 down shaft 20 to secure the implant and suture in the bone hole. More specifically, as shown in FIG. 4A, the screw 42 is advanced by holding thumb pad 50 as the driver handle 22 is turned clockwise. An Arthrex FiberLink and an Arthrex Scorpion suture passer 44, are used to shuttle both tails of the suture tape through the rotator cuff 34 simultaneously. This procedure is followed for both medial swivel anchors.

Figure 5:
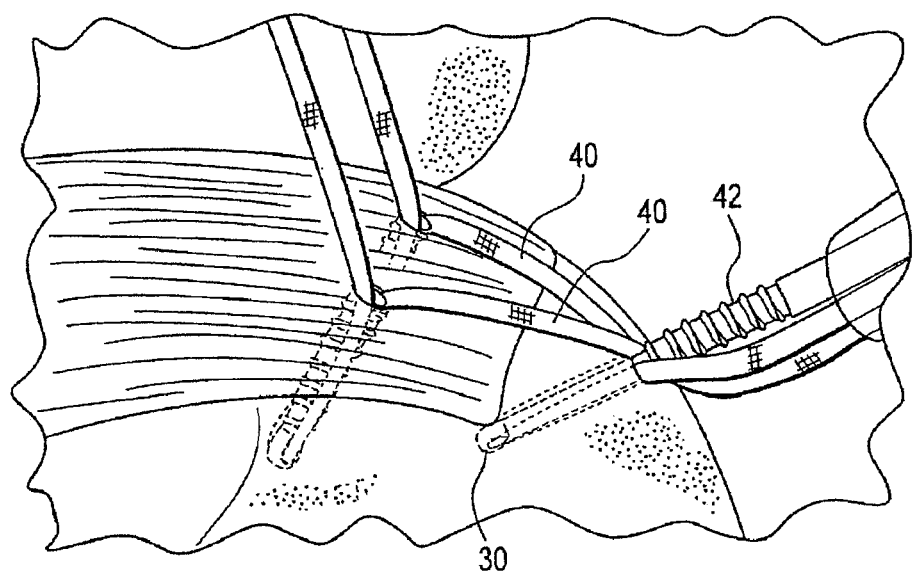
Figure 6:
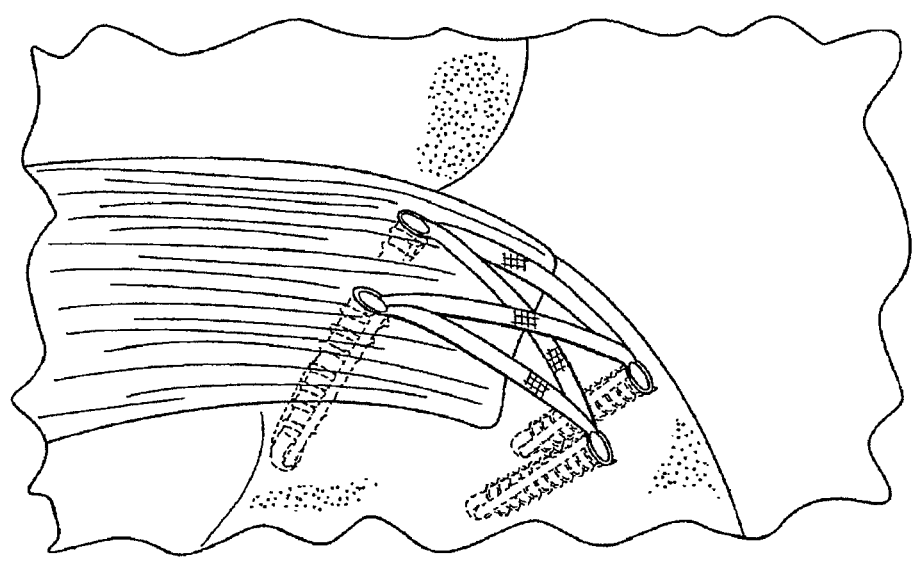
Figure 13:
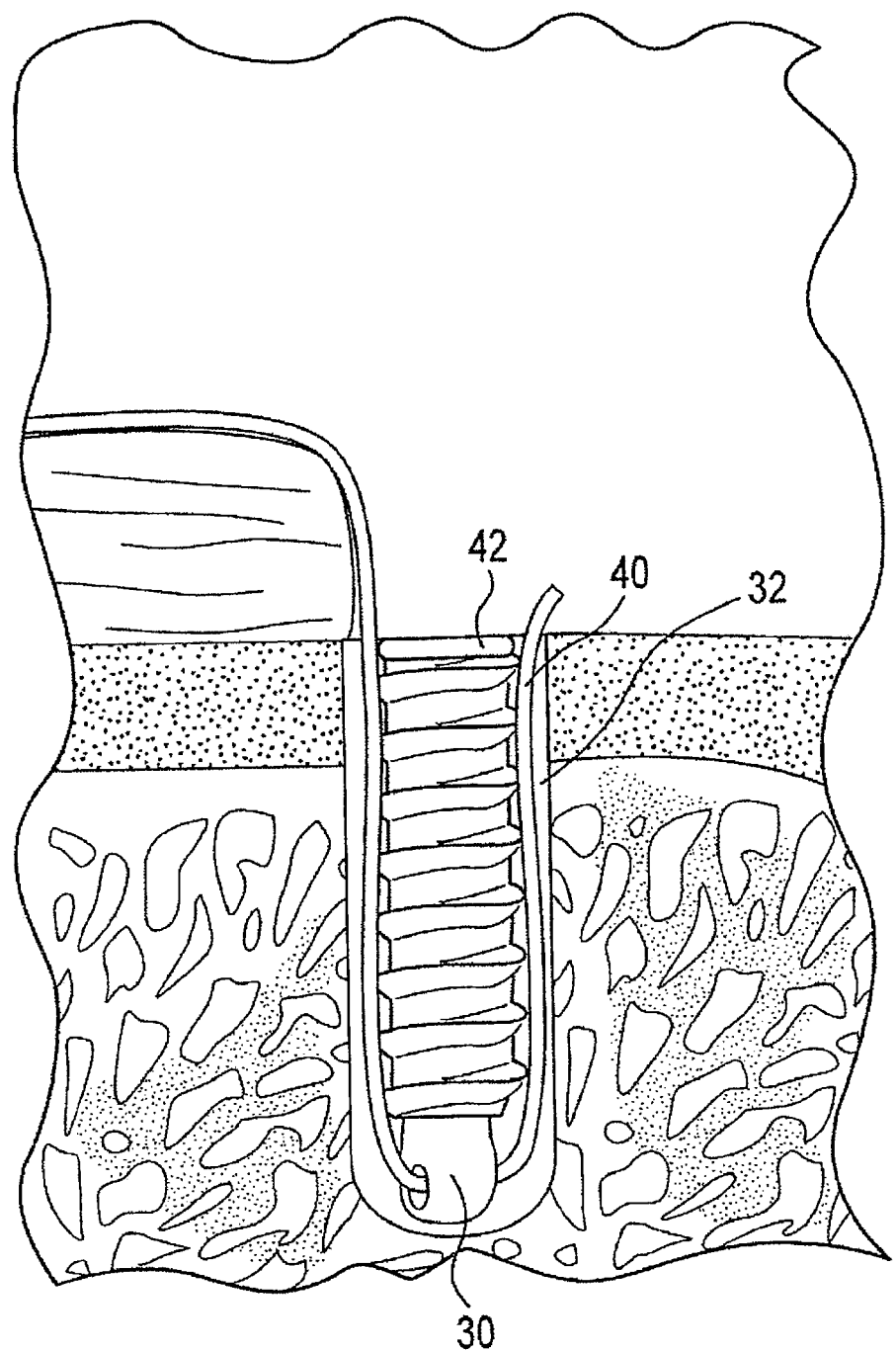

Referring to FIG. 5, one tail of suture tape 40 from each medial swivel anchor is retrieved and loaded through the eyelet of another swivel implant 30, and that implant is installed in then inserted into a preformed lateral bone socket. The tension of the suture tape 40 is adjusted if necessary. The swivel anchor driver is then rotated in clockwise direction as before to advance the screw 42 over the implant to complete insertion. This step is repeated in another lateral bone socket with the other tails of suture tape from each medial anchor. The tails of the suture tape 40 are then cut, one at a time, to complete the construct as shown in FIG. 6. The method is analogous to the method disclosed in U.S. Pat. No. 8,012,174, the entire disclosure of which is incorporated by reference herein. FIGS. 12 and 13 provide additional illustrations of the swivel anchor assembly and the anchor inserted in a bone socket, respectively.

Figure 10:
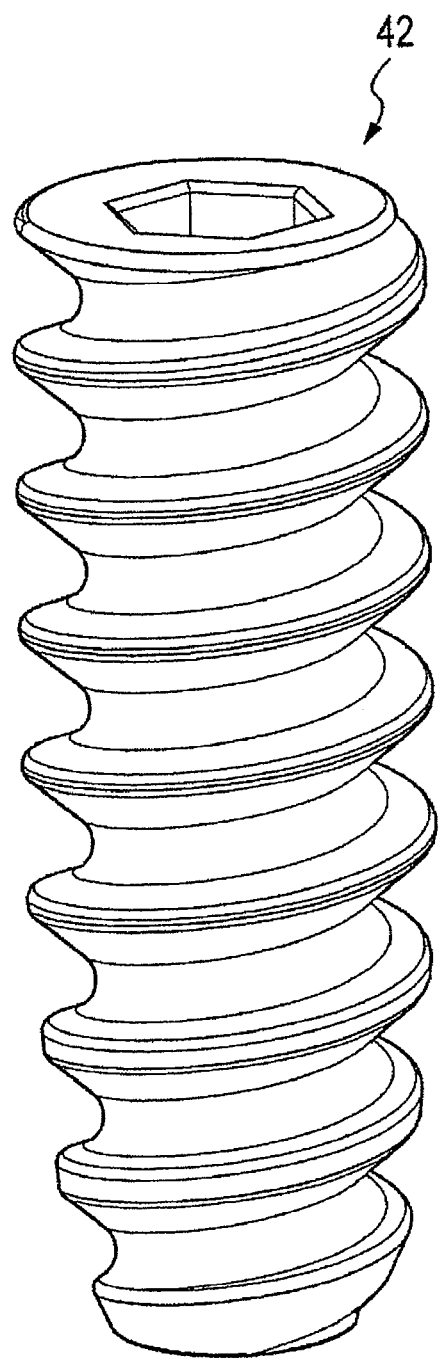
FIG. 10 is an enlarged view of the fixation device (cannulated screw) used in the present invention.
Figure 11A:
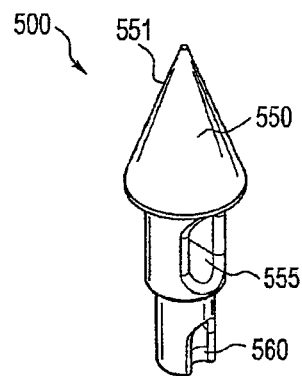
FIGS. 11A-11E illustrate various views of a swivel anchor with a metal tip which avoids the need to pre-drill a hole in bone.
Figure 11B:
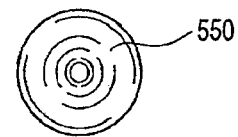
Figure 11C:
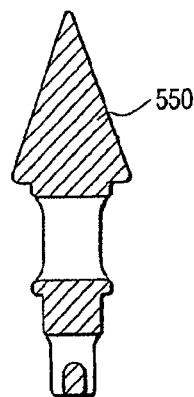
Figure 11D:
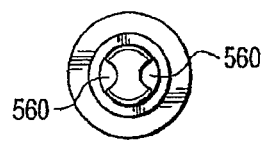
Figure 11E:
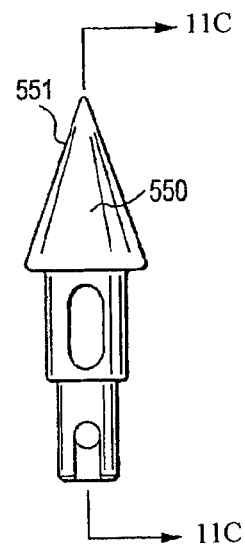

The swivel anchor and instruments of the present invention are now described in greater detail. As shown in FIGS. 7A-7F, a driver 68 is used to install the knotless fixation devices with a swiveling implant. Driver 68 features a thin cannulated rod 20 passing slidably and rotatably through a cannulated driver assembly. The tip of thin cannulated rod 20 is adapted to accept swivel anchor implant 42 within the cannulation at its tip, preferably via a snap fit. Cannulated rod 20 has a hexagonal outer surface for receiving anchor body (preferably a screw) 42 having a corresponding cannulation. FIG. 10 illustrates a detailed view of the cannulated screw 42.

Figure 7A:
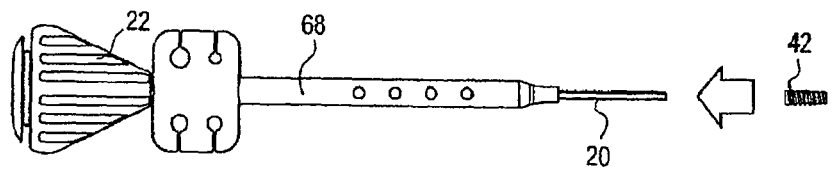
FIGS. 7A-7G illustrate various views of the driver assembly of the present invention.
Figure 7B:
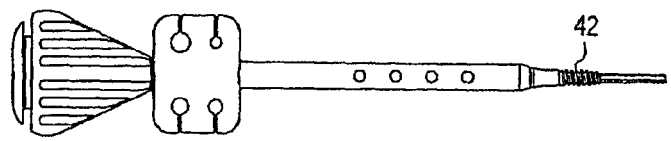
Figure 7C:
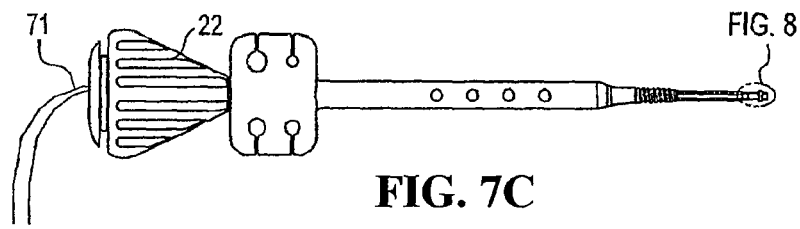
Figure 7D:
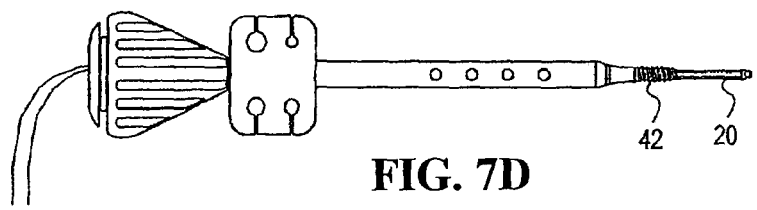
Figure 7E:
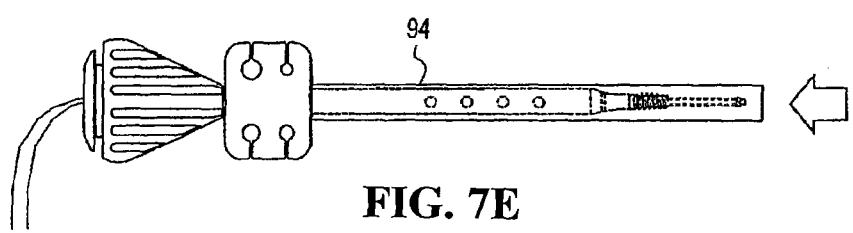
Figure 7F:
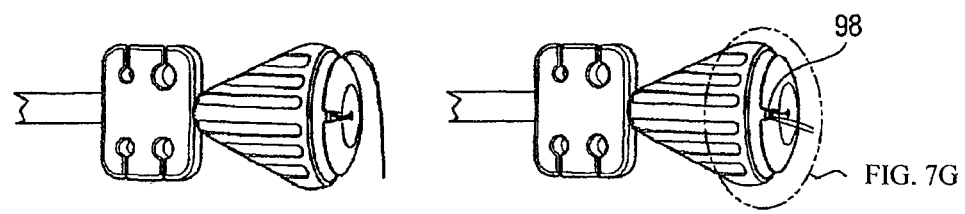
Figure 7G:
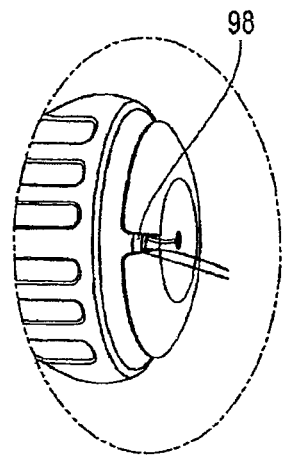
Figure 8:
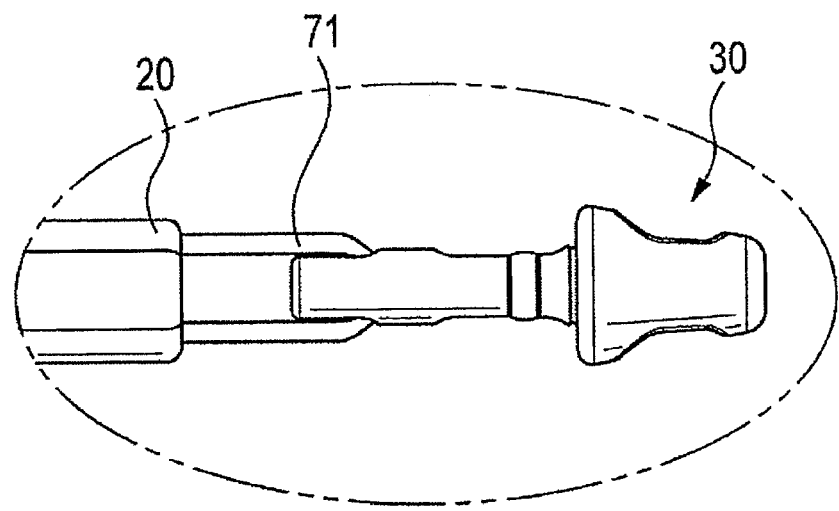
FIGS. 8 and 9 illustrate the swivel implant and traction suture.
Figure 9:
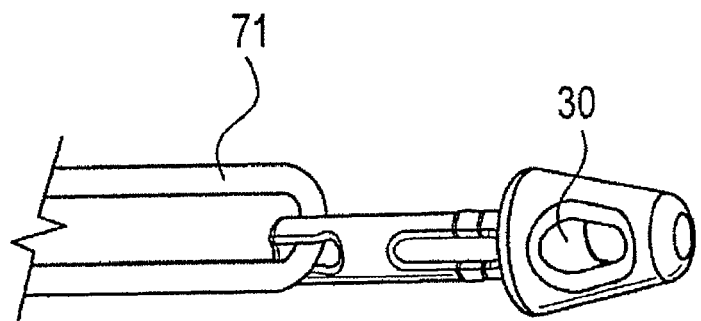

During installation of the knotless anchor having a swiveling implant 30, the screw 42 is first inserted onto cannulated rod 20 of the driver 68. As shown in FIGS. 7A and 7B, screw 42 is loaded onto rod 20 and then fully seated on the shaft end of the driver. FIG. 7C illustrates the swivel anchor implant 30. As shown in FIGS. 8-9, traction sutures 71 extending from the proximal end of the swivel anchor implant 30 are threaded through the cannulation of the driver 68 (see also FIG. 7C). These traction sutures 71 prevent inadvertent separation of the implant 30 from the driver during insertion, but they can be used subsequently for additional tie-down of the tendon after the driver is removed. Subsequently, the swivel anchor implant 30 is seated on the driver tip and until advanced until it snaps onto place (FIG. 7D). A protective tube 94 (FIG. 7E) may be placed over the tip of the assembly for shipping purposes. The traction sutures 71 may be looped around the driver handle, as shown in FIGS. 7F and 7G, and secured in a cleat 98 to prevent the implant 200 from becoming prematurely detached from the driver.

The knotless fixation device of the present invention advantageously minimizes or eliminates the need to tie knots. The use of such a swivel anchor also provides secure fixation of the suture construct—the secure suture construct results from the suture being pushed into a hole and held tightly by an anchors.

In the preferred embodiment of the present invention, as mentioned above, suture tape is used with the swivel anchor to fix tissue to bone. However, the swivel anchor of the present invention can be used with any type of flexible material or suture. In another preferred embodiment, an allograft or biological component may be used instead of suture or tape. The allograft or biological component may be comprised of tendon or pericardium, for example, which provides improved tissue repair. In yet additional embodiments, any combination of suture, suture tape, and allograft or biological component may be employed, depending on the characteristics of the specific surgical repair and/or as desired.

FIGS. 11A-11E illustrate a swivel implant 500 which is provided with a pointed metal tip to facilitate insertion of the implant without the need to pre-drill or pre-form a hole in the bone. The conical configuration of the most distal end pointed tip 550 allows the implant to undergo a self-punching operation, eliminating any need to pre-drill a hole in the bone. End 560 of the implant 500 is opposite the tip 550. The conical configuration of the most distal end of the pointed tip implant 550 also provides suture fixation strength, as well as accelerated graft/tendon healing to bone. The pointed tip implant 550 may be detachable from the driver.

As illustrated in FIGS. 11A-11E, pointed tip implant 500 is provided with a metal tip 550 and an eyelet or aperture 555 for receiving suture or suture tape. Pointed tip implant 550 is also provided, at its most distal end, with a conical portion 551 which allows direct advancement of the implant (by simply tapping the device with a mallet, for example) without the formation of a pilot hole in bone. Preferably, the conical portion 551 of the implant is formed of titanium or titanium alloy. In a preferred embodiment, eyelet or aperture 555 is also formed of titanium or similar material, to withstand impaction forces during the graft fixation procedure.

FIGS. 14-16 illustrate various views of another exemplary fixation device 600 of the present invention that is employed in conjunction with the driver assembly 68 and a swivel anchor or implant of the present invention (such as the swivel anchor implant 30 or the swivel implant 500 described above). The fixation device 600 is similar to the fixation device (swivel anchor implant) 42 of FIG. 10, but differs from it in that the fixation device 600 is provided with a plurality of openings or fenestrations 605 provided on the outer surface of the body of the device. The openings or fenestrations 605 may have various dimensions and geometries provide multiple pathways for w blood to pass through the device (i.e, through the fenestrations and up through the cannulation) and, therefore, to the repair site to promote healing. The fenestrations also promote in-growth of bone. The decreased mass of the device 600 (resulting from the fenestrations) further promotes healing and in-growth.

Preferably, the fixation device 600 is preloaded on the driver 68. As described above with reference to the three exemplary embodiments, the fixation device 600 is advanced into the bone socket by holding the thumb pad 50 as the driver handle 22 is turned clockwise. When the fixation device 600 is fully seated, the shaft of the anchor implant 30 or the swivel implant 500 is fully engaged by the fixation device 600 to optimize the stability of the swivel anchor construct (composed of swivel anchor or implant 30, 500 and fixation device 600).

As illustrated in FIGS. 14-16, the fixation device 600 includes a cannulated body 612 in the form of a tapered cylinder having a proximal end 613 and a distal end 615. The body 612 can have outer threads 614, as seen FIG. 16. A continuous thread 620 wraps around cannulated body 612 in a clockwise direction, as shown. As shown in FIG. 15, the distal end 615 of the interference screw 600 terminates in an exposed, flat surface provided with an opening 616. The proximal end 613 of the interference screw 600 terminates in a drive socket 617 that allows a driver to seat snuggly in the drive socket to allow manipulation and installation of the interference screw into the bone socket, while fully engaging the shaft of the swivel anchor 30 or swivel implant 500 (as detailed above with reference to interference screw 42). As shown in FIG. 16, drive socket 617 may be configured to be used with a traditional hex drive screwdriver. Although the drive socket 617 has been described as having hexagonal shape, the drive socket may also have a Delta drive configuration or a cruciform shape, among others, that allows the driver to rotationally engage the interference screw, to turn simultaneously with the driver.

The fixation device 600 of the present invention may be formed of a biocompatible and/or biosorbable material. Preferably, screw 600 is formed of a bioabsorbable material, such as poly-(L-lactic acid) (PLLA), poly-(D,L-lactide), and poly glycolic acid (PGA), for example, or other bioabsorbable, non-metallic materials, which may be especially tailored for hardness, tensile strength and compressive strength. Alternatively, fixation device 600 may be formed of titanium, titanium alloy, stainless steel or stainless steel alloy. Other biocompatible materials which could be used include plastics, allograft bone and inert bone substitute materials.

A growth material may be advanced through the cannulated driver and into the screw 600 by employing a plunger, for example. As the driver is pulled out, the plunger pushes the flow material through the cannulation of the driver and into the body of the screw 600. The growth material will subsequently harden to allow better fixation of the interference screw 600 against the bone and the shaft of the swivel anchor 30 or swivel implant 500.

The growth material may be any solid, semi-solid, viscous, flowable, gel or elastic composition or mixture that allows its easy manipulation and insertion into the body 612 of the interference screw 600. The growth material may contain growth factors such as autogenous growth factors, for example platelet-rich plasma (PRP), optionally in combination with hyaluronic acid (HY acid) and/or with a coagulant such as thrombin.

The term "growth factor" as used in the present application is intended to include all factors, such as proteinaceous factors, for example, which play a role in the induction or conduction of growth of bone, ligaments, cartilage or other tissues associated with bone or joints. In particular, these growth factors include bFGF, aFGF, EGF (epidermal growth factor), PDGF (platelet-derived growth factor), IGF (insulin-like growth factor), TGF-$\beta$. I through III, including the TGF-$\beta$. superfamily (BMP-1 through 12, GDF 1 through 12, dpp, 60A, BIP, OF).

Optionally, the growth material may comprise additional osteoconductive bone adhesives, calcium carbonate, fatty acids, lubricants, antiseptic chemicals and/or antibiotics. In this case, other solution excipients such as buffer salts, sugars, anti-oxidants and preservatives to maintain the bioactivity of the growth material and a proper pH of the growth material may be also employed. The additional lubricants and/or the antiseptic and/or the antibiotic will typically be present in the growth material in a predetermined concentration range, which will be dependent upon the particular bone site and application, as well as the specific activity of the antiseptic and/or the antibiotic.

Although the present invention has been described in relation to particular embodiments thereof, many other variations and modifications and other uses will become apparent to those skilled in the art. It is preferred, therefore, that the present invention be limited not by the specific disclosure herein.

What is claimed is:

1. A method of knotless tissue fixation comprising:
   securing a suture to tissue to be fixated;
   inserting an implant, that is connected to the suture, into bone by using a driver, wherein when the implant and a cannulated fixation device that is longer axially than the implant are loaded on the driver, the cannulated fixation device is configured to swivel relative to the implant and has a first width representing a maximum outer width of the entire cannulated fixation device;
   anchoring the suture and the implant to the bone by rotating and advancing the cannulated fixation device on the driver and into the bone; and
   removing the driver, such that the suture, the implant, and the cannulated fixation device are secured and the tissue is fixated to the bone without tying any knots in the suture during the knotless tissue fixation, and while the maximum outer width of the entire cannulated fixation device remains constant at the first width.

2. The method of claim 1, wherein the cannulated fixation device is an interference screw.

3. The method of claim 1, wherein the driver includes a cannulated rod passing slidably and rotatably through a cannulated driver assembly of the driver, the cannulated rod having a tip adapted to accept the implant, to allow the implant to be loaded onto the rod and be fully seated on an end of the shaft of the driver.

4. The method of claim 3, wherein the cannulated rod has a hexagonal outer surface for receiving a corresponding inner surface of said cannulated fixation device.

5. The method of claim 3, wherein the cannulated driver assembly of the driver includes a handle and an opposite operative end, and the operative end is configured to engage the cannulated fixation device.

6. The method of claim 5, wherein the tip of the cannulated rod that is adapted to accept the implant is distal to the operative end of the cannulated driver assembly.

7. The method of claim 1, further comprising connecting the suture, that is attached to the tissue, to the implant.

8. The method of claim 1, wherein when the suture is anchored to the bone, the implant and the cannulated fixation device fit together in axial alignment.

9. The method of claim 1, wherein when the suture is anchored to the bone, the implant and the cannulated fixation device engage one another via a snap fit connection.

10. The method of claim 1, wherein the implant is detachable from the cannulated fixation device.

11. The method of claim 1, wherein the suture comprises a plurality of suture loops.

12. The method of claim 1, wherein at least part of the implant is wider than at least part of the cannulation through the cannulated fixation device, forming a rigid abutment therebetween that prevents the implant from passing entirely through the cannulated fixation device.

13. The method of claim 1, wherein the implant comprises a central portion and two arms extending from the central portion.

14. The method of claim 13, wherein the two arms extend distally from the central portion to form a forked tip of the implant.

15. The method of claim 14, wherein the forked tip of the implant is configured to capture the suture attached to the tissue.

16. The method of claim 1, wherein the suture is anchored to the bone by rotating and advancing the cannulated fixation device without excessive rotation of the implant and suture.

17. The method of claim 1, wherein the implant is releasably attachable to a distal end of the driver.

18. The method of claim 17, wherein at least part of the implant is insertable into the distal end of the driver.

19. The method of claim 17, wherein the implant is releasably attached to the distal end of the driver via a snap fit connection.

20. The method of claim 1, wherein, when the implant is connected at a first end of the cannulated fixation device, the implant does not extend past an opposite second end of the cannulated fixation device.

21. The method of claim 1, wherein the implant is inserted into the bone prior to insertion of the cannulated fixation device.

22. The method of claim 1, wherein at least part of the implant is insertable axially into the cannulated fixation device.

23. The method of claim 1, wherein when the implant and the cannulated fixation device are loaded on the driver, the implant remains separable from the cannulated fixation device.

24. The method of claim 1, wherein when the implant is inserted into the bone, the suture does not form a closed loop around or through the tissue to which the suture is secured.

25. A method of knotless tissue fixation comprising:
securing a suture to tissue to be fixated;
inserting an implant, that is connected to the suture, into bone by using a driver, wherein when the implant and a cannulated fixation device that is longer axially than the implant are loaded on the driver, the cannulated fixation device is configured to swivel relative to the implant and has a first width representing a maximum outer width of the entire cannulated fixation device; and
anchoring the suture to the bone by rotating and advancing the cannulated fixation device on the driver and into the bone,
wherein the suture, the implant, and the cannulated fixation device are secured and the tissue is fixated to the bone without tying any knots in the suture during the knotless tissue fixation, and while the maximum outer width of the entire cannulated fixation device remains constant at the first width, and
wherein at least part of the implant is wider than at least part of the cannulation through the cannulated fixation device, forming a rigid abutment therebetween that prevents the implant from passing entirely through the cannulated fixation device.

26. The method of claim 25, wherein the driver includes a cannulated rod passing slidably and rotatably through a cannulated driver assembly of the driver, the cannulated rod has a tip adapted to accept the implant, to allow the implant to be loaded onto the rod and be fully seated on an end of the shaft of the driver.

27. The method of claim 26, wherein the driver includes an operative end that is opposite a handle thereof, and the operative end is configured to engage the cannulated fixation device.

28. The method of claim 27, wherein the tip of the cannulated rod that is adapted to accept the implant is distal to the operative end of the cannulated driver assembly.

29. A method of knotless tissue fixation comprising:
securing a suture to tissue to be fixated;
inserting an implant, that is connected to the suture, into bone by using a driver, wherein when the implant and a cannulated fixation device that is longer axially than the implant are loaded on the driver, the cannulated fixation device is configured to swivel relative to the implant and has a first width representing a maximum outer width of the entire cannulated fixation device; and
anchoring the suture to the bone by rotating and advancing the cannulated fixation device on the driver and into the bone,
wherein the implant comprises a surface configured to engage and prevent proximal movement of the suture, and
wherein the suture, the implant, and the cannulated fixation device are secured and the tissue is fixated to the bone without tying any knots in the suture during the knotless tissue fixation, and while the maximum outer width of the entire cannulated fixation device remains constant at the first width.

30. The method of claim 29, wherein the driver includes a cannulated rod passing slidably and rotatably through a cannulated driver assembly of the driver, the cannulated rod has a tip adapted to accept the implant, to allow the implant to be loaded onto the rod and be fully seated on an end of the shaft of the driver.

31. The method of claim 30, wherein the driver includes a handle at the proximal end thereof and an operative end at the distal end thereof, and the operative end is configured to engage the cannulated fixation device.

32. The method of claim 31, wherein the tip of the cannulated rod that is adapted to accept the implant is distal to the operative end of the cannulated driver assembly.

* * * * *